United States Patent [19]

Tanaka

[11] Patent Number: 5,702,921
[45] Date of Patent: Dec. 30, 1997

[54] **EXPRESSION OF BIOLOGICALLY ACTIVE HUMAN C-REACTIVE PROTEIN IN *ESCHERICHIA COLI***

[75] Inventor: Toshio Tanaka, Shiga-ken, Japan

[73] Assignee: Orienta Yeast Co., Ltd., Tokyo, Japan

[21] Appl. No.: 621,897

[22] Filed: Mar. 26, 1996

Related U.S. Application Data

[63] Continuation of Ser. No. 223,954, Apr. 6, 1994, abandoned.

[30] Foreign Application Priority Data

Apr. 27, 1993 [JP] Japan .................................. 5-122209

[51] Int. Cl.$^6$ .................. C12P 21/02; C12N 15/70; C12N 15/71; C12N 1/21
[52] U.S. Cl. .................. 435/69.6; 435/69.7; 435/69.8; 435/252.33; 435/320.1
[58] Field of Search .................. 435/243, 252.1, 435/252.3, 252.33, 172.1, 172.3, 320.1, 41, 69.6, 69.7, 69.8; 536/23.1, 23.2, 24.1

[56] References Cited

U.S. PATENT DOCUMENTS

| | | | |
|---|---|---|---|
| 5,246,839 | 9/1993 | Horikoshi et al. | 435/69.1 |
| 5,547,931 | 8/1996 | Potempa | 514/2 |

FOREIGN PATENT DOCUMENTS

| | | |
|---|---|---|
| 0216080 | 4/1987 | European Pat. Off. . |
| 62-258390 | 11/1987 | Japan . |
| 62-258399 | 11/1987 | Japan . |

OTHER PUBLICATIONS

M. L. Tenchini et al, "Comparison of sequence of cDNA clone with other genomic and cDNA sequences for human C-reactive protein", *Inflammation*, Vol. 16, No. 2, Apr. 1992, pp. 93–99.

C. Toniatti et al, "Synergistic trans–activation of the human C-reactive protein promoter by transcription factor HNF-1 binding at two distinct sites", *J. EMBO*, Vol. 9, No. 13, Dec. 1990, pp. 4467–4475.

"Expression in *Escherichia coli* of a Chemically Synthesized Gene for the Hormone Somatostatin", *Science*, Vol. 198, pp. 1056–1063 (1978).

"Preparation of Transforming Deoxyribonucleic Acid by Phenol Treatment", *Biochimica et Biophysica ACTA*, Vol. 72, No. 4, pp. 619–629 (1963).

"Ligation of EcoRl Endonuclease–generated DNA Fragments into Linear and Circular Structures", *Journal of Molecular Biology*, Vol. 96, pp. 171–184, (1974).

Abstract of: *Protein, Nucleic Acid and Enzyme*, Vol. 29, pp. 294–306 (1986).

"Calcium–Dependent Bacteriophage DNA Infection", *Journal of Molecular Biology*, Vol. 53, pp. 159–162 (1970).

"Sequence Diversity among Related Genes for Recognition of Specific Targets in DNA Molecules", *Journal of Molecular Biology*, Vol. 166, pp. 1–19 (1983).

"One–step Preparation of Competent *Escherichia coli*: Transformation and Storage of Bacterial Cells in the Same Solution", *Proc. Natl. Acad. Sci. USA*, Vol. 86, pp. 2172–2175 (1989).

Lei et al, J. of Biol. Chem. 260(24), pp. 13377–13383, Oct. 1985.

Woo et al, J. of Biol. Chem. 260(24), pp. 13384–13388, Oct. 1985.

Sambrook et al., Molecular Cloning: A laboratory manual, pp. 1.74–1.81;pp. 17.10–17.11, 1989.

Oka et al., PNAS (USA) 82, pp. 7212–7216, Nov. 1985.

Kobayashi et al., J. of Bacteriology 166(3), pp. 728–732, Jun. 1986.

*Primary Examiner*—Mindy Fleisher
*Assistant Examiner*—Terry A. McKelvey
*Attorney, Agent, or Firm*—Burns, Doane, Swecker & Mathis

[57] ABSTRACT

The present invention relates to a plasmid possessing the restriction enzyme map shown in FIG. 1, and this plasmid is largely characterized in that the kil gene is linked downstream from the human CRP (C-reactive protein) gene. Using this plasmid, it is possible to produce large amounts of human CRP by extracellular secretion.

16 Claims, 5 Drawing Sheets

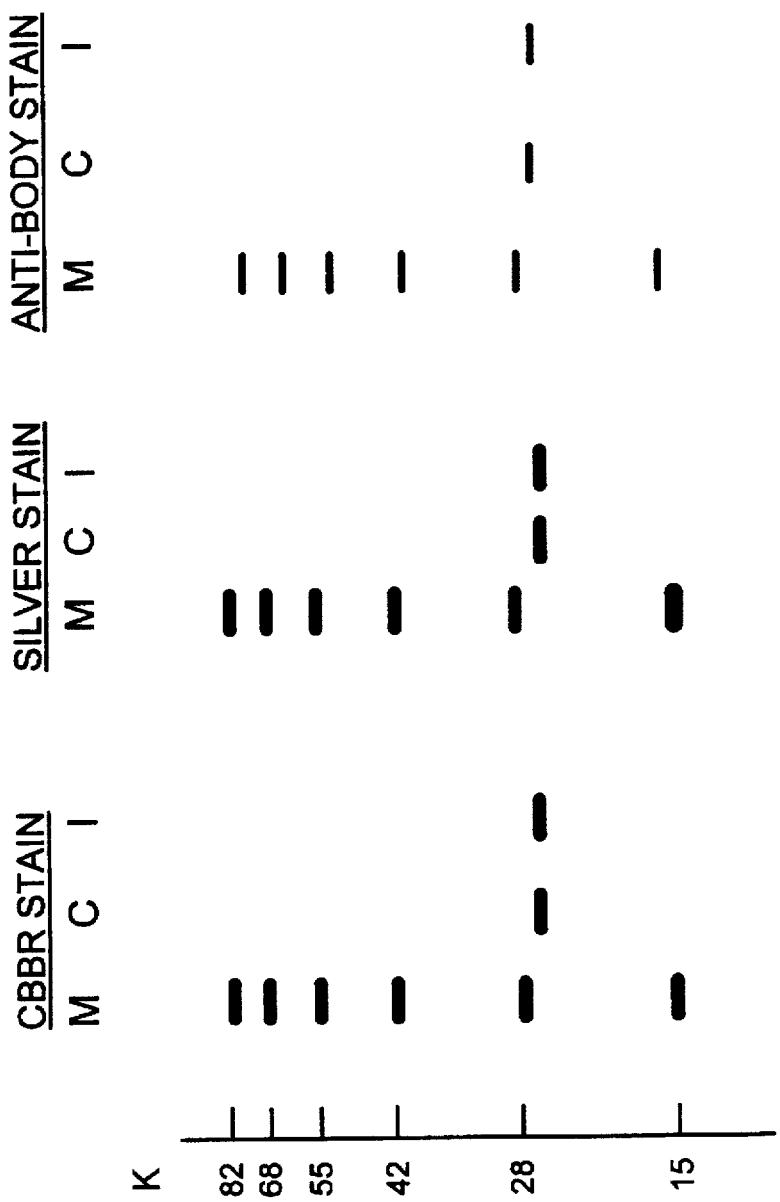

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GCTGCAGTCA GGGCCACAGC TGGGTTT         2 7

( 2 ) INFORMATION FOR SEQ ID NO:2:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGAATTCATG CAGACAGACA TGTCGAGGAA GGCTTTTGTG TTTCCCAAA                    49

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

Met Lys Gln Ser Thr Ile Ala Leu Ala Leu Leu Pro Leu
1               5                   10

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AATTCATGAA ACAAAGCACT ATTGCACTGG CACTCTTACC GTTA                        44

( 2 ) INFORMATION FOR SEQ ID NO:5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

AAACAGTAAC GGTAAGAGTG CCAGTGCAAT AGTGCTTTGT TCATG                       46

( 2 ) INFORMATION FOR SEQ ID NO:6:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

Leu Phe Thr Pro Val Thr Lys Ala Gln Thr Asp Met Ser Arg Lys
1               5                   10                  15

( 2 ) INFORMATION FOR SEQ ID NO:7:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

CTGTTTACCC CTGTGACAAA AGCCCAAACA GATATGTCAA GAAA                        44

( 2 ) INFORMATION FOR SEQ ID NO:8:

( i ) SEQUENCE CHARACTERISTICS:
         ( A ) LENGTH: 42 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:8:

AGCTTTTCTT GACATATCTG TTTGGGCTTT TGTCACAGGG GT                                    42

EXPRESSION OF BIOLOGICALLY ACTIVE HUMAN C-REACTIVE PROTEIN IN ESCHERICHIA COLI

This application is a continuation of application Ser. No. 08/223,954, filed Apr. 6, 1994, now abandoned.

DETAILED DESCRIPTION OF THE INVENTION

1. Field of the Industrial Use

The present invention relates to biotechnology, and more specifically, it relates to a novel plasmid carrying the gene for human CRP (C-reactive protein), to novel microorganisms, for example those belonging to *Escherichia coli*, which have been transformed with the plasmid, as well as to a novel method for the production of human CRP by the culturing of the above transformant.

According to the present invention there has been established a method for the industrial production of human CRP, and since the purity of the resulting human CRP is extremely high, it may be used more effectively in the fields of diagnosis and clinical examination, as well as medicines.

2. Prior Art

Human CRP is produced in the liver upon stimulation by as yet unidentified stimulating substances resulting from bacterial infection, histological ischemic disorder, malignant tumors, etc., and upon reaching the site of inflammation, it binds to the phospholipids of the membranes of cells which have undergone necrosis, inducing such biological changes as the activation of complement, the suppression of platelet aggregation, the acceleration of various lymphatic functions, and the acceleration of the functions of macrophages, by which the pathologic products produced in the body by the inflammation are removed.

In the field of clinical examination, assays of CRP levels in the blood are conducted by methods in which anti-CRP antiserum is added to test serum thought to contain CRP, such as the single immunodiffusion method and the capillary method. However, the presently used abdominal dropsy-derived antigen is prepared through purification for removing serum components including SAP (serum amyloid P component) whose amino acid sequence is highly homologous with that of CRP, to such an extent that they do not interfere with the antigen, and so requires many purification steps, thus increasing production costs. In addition, when making measurements of CRP in the blood using antiserum or IgG obtained by animal immunization using as the antigen CRP which is insufficiently pure, being mixed with serum components, it has been difficult to make accurate assays because of the background antibodies against the serum components such as SAP which are not completely removed by the purification.

Consequently, as antigen CRP for use in the field of clinical examination it has been greatly desired to have highly pure and economical CRP which contains no serum components such as SAP.

On the other hand, bacteria belonging to the genus Escherichia produce absolutely no CRP.

Also, plasmids useful for recombinant DNA and microorganisms transformed therewith are well known. For example, in *Science*, 198, 1056, 1978, there is described the production of an animal protein in *Escherichia coli* into which has been introduced a plasmid comprising lactose promoter linked to plasmid pBR322.

However, there has been no description whatsoever regarding plasmids carrying the human CRP gene or microorganisms transformed therewith, nor any publication reporting success in creating them.

Subject Matter to be Solved by the Invention

In the field of clinical examination, when the CRP level of blood is assayed, even a trace residue of serum components (particularly SAP) in the antigen CRP used for the preparation of the antibodies causes the resulting antiserum to contain antibodies against the residual serum components, producing background in the measured value. Consequently, when preparing antigen CRP from human-derived-starting materials, it has been difficult to prepare anti-CRP antibodies which allow an accurate assay of the CRP level in the blood.

BRIEF DESCRIPTION OF THE DRAWINGS

FIG. 5 shows a comparison of the purities of purified recombinant human CRP and naturally occurring human CRP.

DETAILED DESCRIPTION OF THE INVENTION

Figure 1:
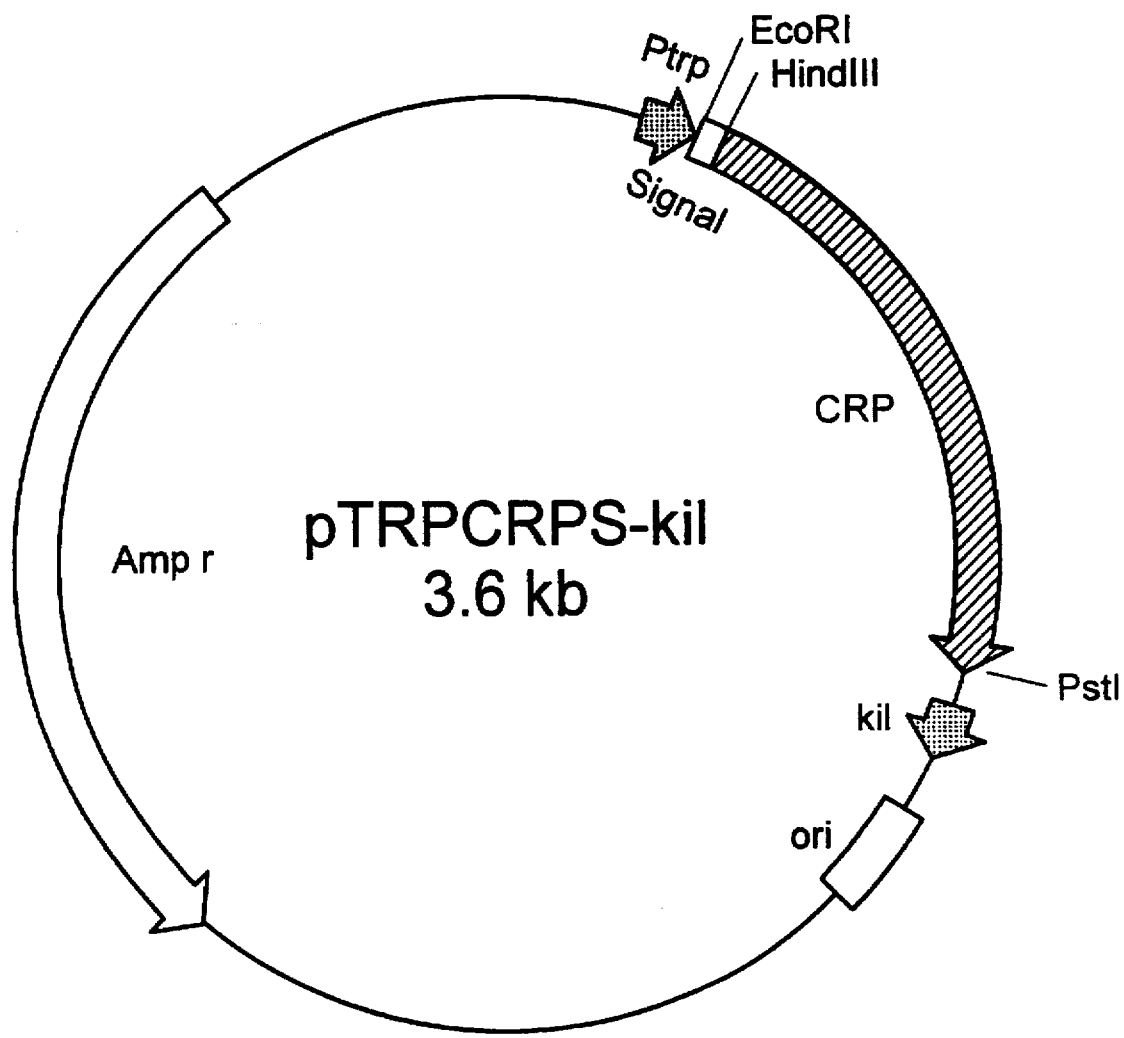
FIG. 1 is a restriction enzyme map of the human CRP expression vector pTRPCRPS-kil.

Here, the present inventor, as a result of diligent research regarding the preparation of highly pure antigen CRP which is free of serum components by the genetically engineered preparation of human CRP, have succeeded in preparing recombinant CRP which is absolutely identical to naturally occurring CRP in terms of both protein chemistry and immunology, by the extracellular secretion expression of CRP by *E. coli*.

In other words, the present inventor has discovered that the gene for human CRP may be amplified from human placenta-derived chromosomal DNA using the PCR (Polymerase Chain Reaction) method and cloned in a plasmid capable of expressing it and that *Escherichia coli* transformed with this plasmid produces large amounts of human CRP, that this recombinant CRP has an amino acid sequence absolutely identical to that of the naturally occurring form and binds with phosphorylcholine in the presence of calcium ion in the same manner as the naturally occurring form, and that by employing the affinity purification method using a phosphorylcholine-immobilized column, in a single step the CRP is purified to a degree suitable for an antigen.

In addition, further research has been carried out to confirm that anti-CRP antibody, which does not cross react with serum components except for CRP, may be obtained by immunization using the recominant CRP obtained above as the antigen, and thus the present invention has been completed. In other words, the gist of the present invention is the amplification of human chromosomal CRP gene by the PCR method, a recombinant comprising a vector plasmid-linked with CRP gene, and *Escherichia coli* transformed using the recombinant vector plasmid-linked with CRP gene.

The plasmid of the present invention may be obtained, for example, according to the method described in *Biochim. Biophys. Acta.*, 72, 619–629, 1963. The plasmid can be prepared by digesting the human CRP gene, promoter and vector using restriction enzymes described in J. Mol. Biol., 96, 171–184, 1974, and then ligating these using a T4 DNA ligase.

As the above mentioned DNA to serve as the vector may be used DNA of, for example, *Escherichia coli*-derived pBR322, etc. The promoter may be, for example, Taq promoter, tryptophan promoter, λ-pL promoter, λ-pR promoter, lactose promoter, T7 promoter, or the like. The secretion signal peptide may be a signal peptide for for example, *Escherichia coli*-derived alkaline phosphatase, outermembrane protein A, outermembrane protein F or β-lactamase, or the like. Also, the restriction enzyme may be, for example, EcoRI or PstI, and the ligase may be, for example, T4DNA ligase.

The human CRP gene to be used according to the present invention may be amplified by the PCR method using human placenta-derived chromosomal DNA as the template. The primer to be used for the amplification has a base sequence which is constructed based on the base sequence of the human CRP gene. This is introduced into the plasmid vector pTZ18U to prepare a plasmid pTZ-CRP carrying the human CRP gene. A gene for the signal peptide of *E. coli* alkaline phosphatase is prepared by chemical synthesis and ligated upstream of the above mentioned gene to prepare pTZ-CRPS. This plasmid is used to transform *Escherichia coli*, which is then infected with the helper phage M13KO7, and single-stranded DNA is prepared from the culture medium thereof. The base sequence of this DNA is determined by the method described in "PROTEIN, NUCLEIC ACID AND ENZYME", 29, 294–306, 1986. The CRP gene whose base sequence has been confirmed is cut off from pTZ18U, and ligated to the extracellular secretion expression vector pTRP-kil comprising plasmid pBR322 with tryptophan promoter, the plasmid pMB9-derived kil gene, and the Shine-Dalgarno sequence (SD sequence) introduced therein, to obtain the plasmid pTRPCRPS-kil.

The physicochemical characteristics of the plasmid pTRPCRPS-kil will now be presented.

(1) The alkaline phosphatase signal peptide gene of *E. coli* may be attached upstream of the human CRP gene for the extracellular (into the medium) secretion expression of human CRP by the action of the kil gene.

(2) As shown in FIG. 1, cleavability is exhibited for the following restriction enzymes.

| Restriction enzyme | Cleavage sites |
| --- | --- |
| EcoRI | 1 |
| PstI | 1 |
| HindIII | 1 |

(3) The molecular weight is about 2.5 megadaltons.

(4) The human CRP gene of molecular weight approximately 400 kilodaltons is found inserted downstream of the promoter in the same direction.

The *Escherichia coli* according to the present invention is *Escherichia coli* which has been transformed with a recombinant plasmid prepared by linking to a vector plasmid the above mentioned human CRP gene of molecular weight 400 kilodaltons and a promoter upstream therefrom, and the transformation of *Escherichia coli* using this plasmid pTRPCRPS-kil may, for example, be carried out according to the method described in J. Mol. Biol., 53, 159–162, 1970, contacting *Escherichia coli* NM522 with the above mentioned plasmid pTRPCRPS-kil treated with calcium chloride at a temperature of around 0° C.

As an example of *Escherichia coil* transformed in this manner there may be mentioned *Escherichia coli* NM522-pTRPCRPS-kil, into which has been introduced the plasmid pTRPCRPS-kil. This strain is a novel strain unknown to the prior art, and it has been deposited at the National Institute of Bioscience and Human Technology under No. FERM BP-4244.

*Escherichia coli*, NM522-pTRPCRPS-kil was deposited on Mar. 24, 1993 at the National Institute of Bioscience and Human-Technology, Agency of industrial Science and Technology, Minister of International Trade and Industry at 1–3, Higashi 1 Chome, Tsukuba-Shi, Ibarakiken, 305 Japan, and accorded Deposit No. FERM BP-4244.

This strain possesses the same bacteriological characteristics as the publicly known *Escherichia coli* NM522 (see J. Mol. Biol., 166, 1–19, 1983), except for the ability to produce human CRP and resistance to ampicillin. This strain remains safe as it causes no change from non-transmissibility to transmissibility or from non-pathogenicity to pathogenicity.

The carbon source in the nutrition medium to be used for the culturing of *Escherichia coli* according to the present invention may be, for example, a saccharide such as glucose, sucrose, fructose, starch hydrolysate, molasses or spent sulfite liquor-derived saccharide; an organic acid such as acetic acid or lactic acid; or an alcohol, fatty acid or glycerin, etc. which may be utilized by the bacteria to be used, and the nitrogen source to be used may be, for example, an inorganic or organic substance such as ammonium sulfate, ammonium chloride, ammonium phosphate, amino acids, peptone, beef extract, yeast extract, or the like. Furthermore, a commonly used culture medium for bacteria may be used, including inorganic salts of, for example, potassium, sodium, phosphoric acid, zinc, iron, magnesium, manganese, copper, calcium, cobalt, etc., and if necessary also trace amounts of a metal salt, corn steep liquor, vitamins, nucleic acids, etc.

The *Escherichia coli* according to the present invention may be aerobically cultured using such culture mediums, at a temperature of 20°–45° C., preferably 35°–40° C. and optimally 37° C. at a pH of 7.0–7.4, and optimally 7.2.

The human CRP according to the present invention is then collected from resulting culture product, and it may be collected at any stage of the product during the process, including the culture product, separated viable cells, separated and treated cells, crude protein extract, or crude protein. The method of purification here may be any conventional method of protein purification.

The human CRP obtained according to the present invention possess the following physicochemical characteristics.

(1) Binding specificity

Binds to the C-polysaccharide of Pneumococcus, phosphorylcholine, fibronectin, etc. in the presence of calcium ion.

(2) Molecular weight

A pentamer of molecular weight approximately 115,000, consisting of 5 identical subunits of molecular weight approximately 23,000.

A more concrete explanation of the present invention will now be provided with reference to the Examples.

EXAMPLE 1

(a) PCR amplification of human CRP gene

Using human placenta-derived chromosomal DNA (product of CLONTECH Co.), the human CRP gene was amplified with the following two primers [SEQ ID NOS 1 & 2].

5'-GCTGCAGTCAGGGCCACAGCTGGGTTT-3'
5'-GGAATTCATGCAGACAGACATGTCGAGGAAGGCTTTTGTGTTTCCCAAA-3'

The reaction mixture for the amplification was prepared by mixing each of 50 mM KCl, 10 mM Tris-HCl (pH 8.3, 25° C.), 1.5 mM MgCl$_2$, 0.01% (w/v) gelatin and 200 NM each of NTP's, 1 µM of each primers, 1 µg of human chromosomal DNA, and Taq polymerase (product of PERKIN ELMER CETUS Co.) to give 100 µl. The sample was further covered with 100 µl of mineral oil to prevent evaporation.

The reaction conditions were denaturation at 94° C. for 1 minute, annealing at 50° C. for 1 minute and polymerization reaction at 72° C. for 3 minutes. The incubation was performed for 30 cycles.

Figure 2:
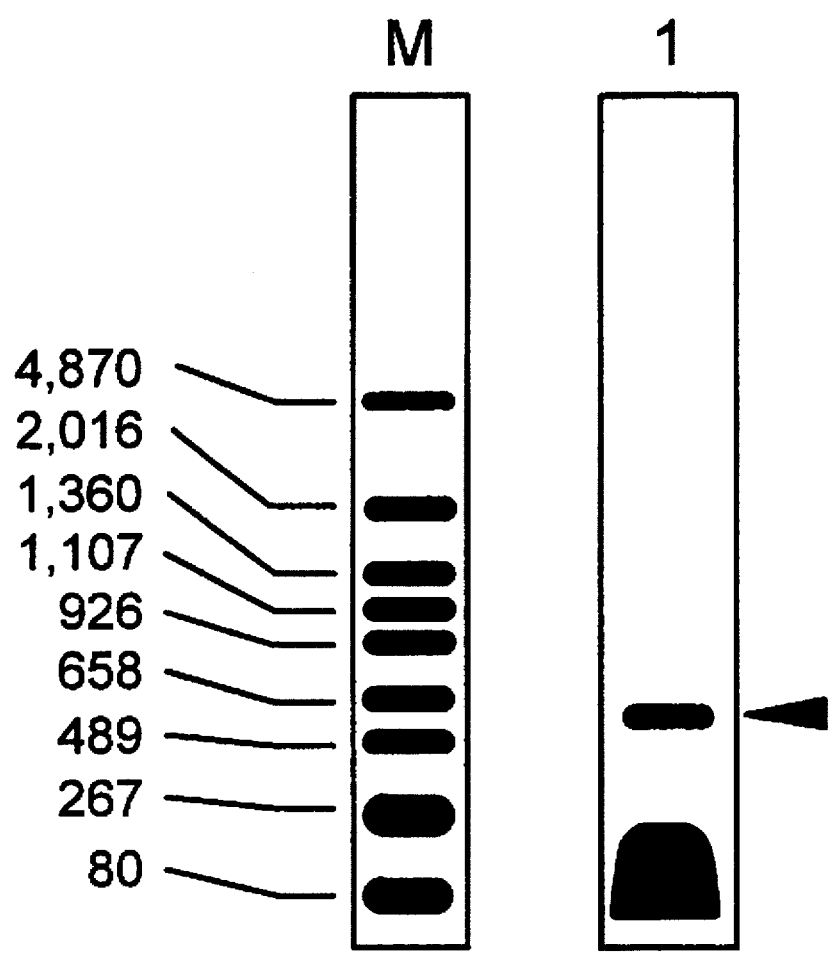
FIG. 2 shows an agarose gel electrophoretic pattern of an amplified human CRP gene.

The contaminant proteins were removed from the reaction solution by phenol extraction. Also, the amplification of the human CRP gene of about 0.64 kb was confirmed by agarose gel electrophoresis. FIG. 2 shows the results of dyeing with ethidium bromide (M: molecular weight marker, 1: recombinant CRP)

(b) Preparation of plasmid pTZ-CRP

One µg each of the commercially available plasmid vectors pTZ18U and pTZ19U [products of USB (United States Biochemicals) Co.] and 2 units each of the restriction enzymes EcoRI (product of Takara Shuzo Co.) and PstI (product of Takara Shuzo Co.) were added to 100 µl of a Tris buffer solution containing 10 mM of MgCl$_2$, 50 mM of NaCl and 1 mM of dithiothreitol and adjusted to a pH of 7.5, and the reaction was conducted at 37° C. for 16 hours. The reaction mixture was then heated at 65° C. for 5 minutes for deactivation of the restriction enzymes and then precipitated with ethanol, and the digested DNA was recovered.

Next, the human CRP gene obtained by the method in (a) was allowed to react at 37° C. for 16 hours in the same solution containing the restriction enzymes as mentioned above, and recovered in the same manner as above. The resulting digested CRP gene was mixed with the digested plasmid DNA, and then allowed to react at 14° C. for 16 hours using T4 DNA ligase (product of Takara Shuzo Co.) in a 70 mM Tris buffer solution containing 7 mM of MgCl$_2$, 20 mM of dithiothreitol and 1 mM of ATP and adjusted to a pH of 7.5 for the religation of the digested DNA, to obtain a plasmid pTZ-CRP carrying the human CRP gene. This plasmid pTZ-CRP was used transformed to E. coli DH5αF'IQ (product of BRL Co.). The resulting transformant was infected with helper phage M13KO7, and cultured. From the resulting culture supernatant single-stranded phage was recovered by polyethylene glycol precipitation. Then, the single-stranded DNA was extracted and purified from the phage by phenol extraction, and the DNA was sequenced using a model 370A DNA sequencer manufactured by ABI Co. The result agreed completely with the known amino acid sequence of human CRP.

(c) Introduction of E. coli alkaline phosphatase signal peptide gene.

Figure 3:
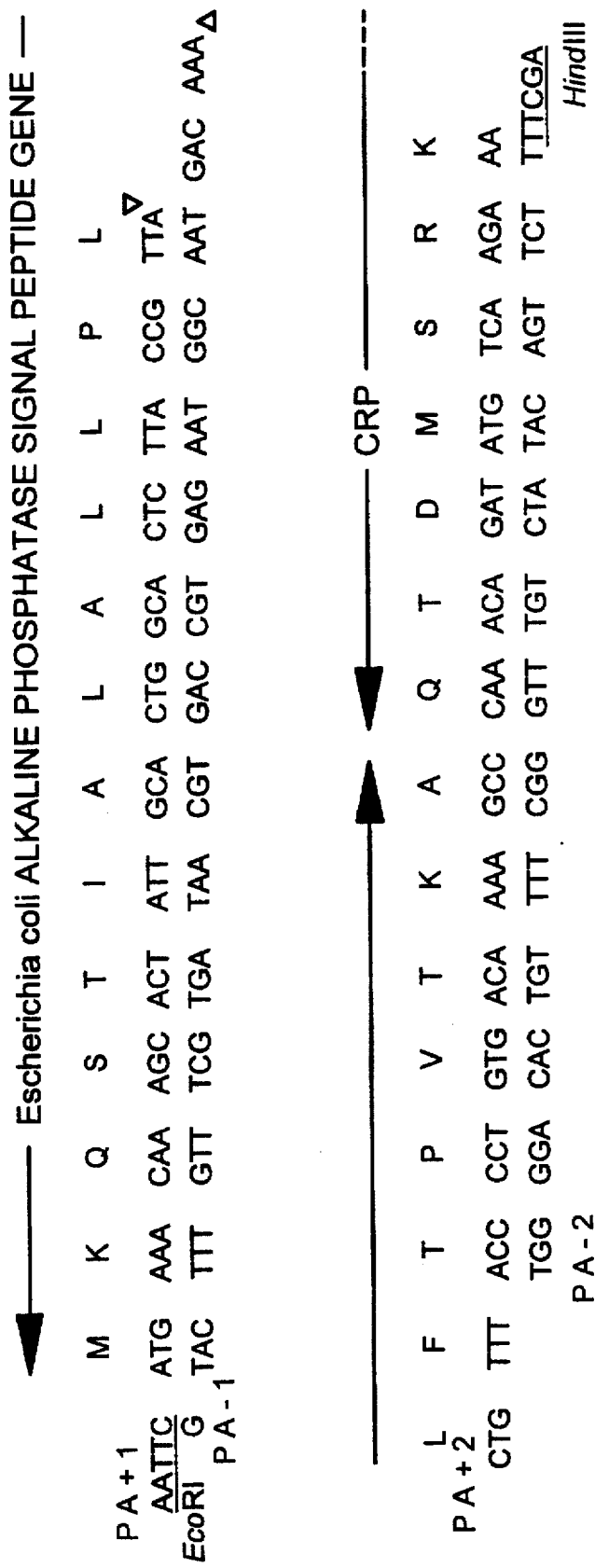
FIG. 3 [SEQ ID NOS: 3–8] shows the chemical synthesis of *Escherichia coli* alkaline phosphatase signal peptide gene.

The E. coli alkaline phosphatase signal peptide gene was chemically synthesized (FIG. 3) using a DNA synthesizer (Model 8750, product of Milligene Biosearch Co.), and it was ligated upstream of the human CRP gene on pTZ-CRP under the same conditions as described above, to prepare pTZ-CRPS.

(d) Preparation of plasmid pTRPCRPS-kil

As the secretion expression vector, pTRP-kil was prepared which contains a tryptophan promoter, restriction sites for EcoRI and PstI at the cloning site and kil gene downstream therefrom at the cloning site and the kil gene downstream therefrom were transcribed by the same tryptophan promoter into a single mRNA strand and was subsequently translated into the respective proteins. The CRP gene including the above mentioned signal peptide was inserted at the polylinker site of the expression vector.

Figure 4:
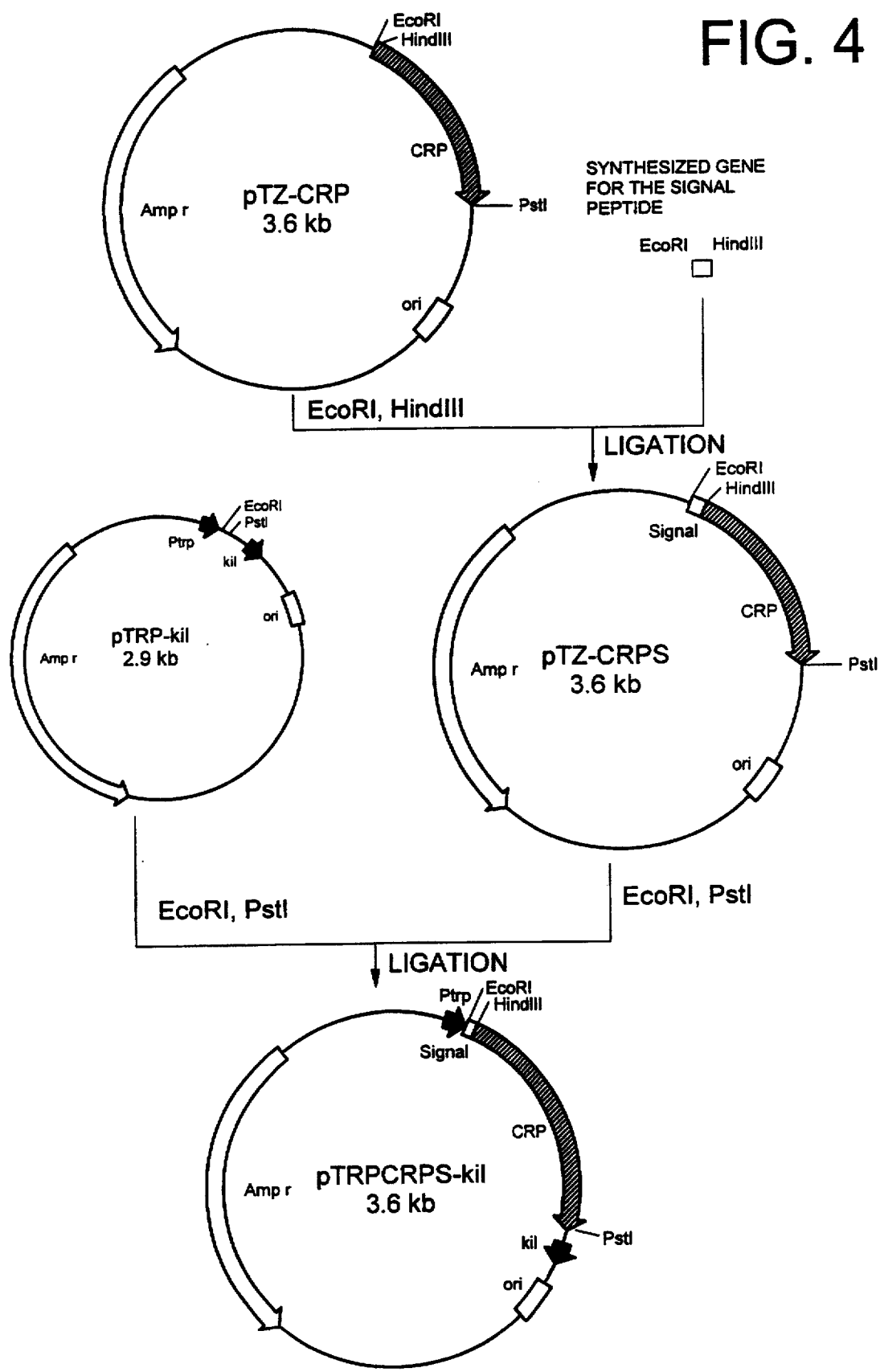
FIG. 4 is a drawing showing the construction of the human CRP expression vector according to the present invention.

One µg of the expression vector pTRP-kil and 2 units each of the restriction enzymes EcoRI (product of Takara Shuzo Co.) and PstI (product of Takara Shuzo Co.) were added to 100 µl of a Tris buffer solution containing 10 mM of MgCl$_2$, 50 mM of NaCl and 1 mM of dithiothreitol and adjusted to a pH of 7.5, and the reaction was conducted at 37° C. for 16 hours. The reaction mixture was then heated at 65° C. for 5 minutes for deactivation of the restriction enzymes and then precipitated with ethanol, and the digested DNA was recovered. Next, the plasmid pTZ-CRPS obtained by the method in (c) was allowed to react at 37° C. for 16 hours in the same buffer solution as above using the restriction enzymes EcoRI and PstI, and the reaction mixture was subjected to agarose gel electrophoresis. The band corresponding to the size of the CRP gene was cut off from the gel and purified using a Gene Clean Kit (BIO 101, Inc.). The thus obtained digested CRP gene was mixed with the plasmid DNA (the digested DNA), and then allowed to react at 14° C. for 16 hours using T4 DNA ligase (product of Takara Shuzo Co.) in a 70 mM Tris buffer solution containing 7 mM of MgCl$_2$, 20 mM of dithiothreitol and 1 mM of ATP and adjusted to a pH of 7.5 for the religation of the digested DNA, to obtain the plasmid pTRPCRPS-kil carrying the human CRP gene (FIG. 4).

EXAMPLE 2

The transformation of E. coli NM522 was carried out using the plasmid pTRPCRPS-kil obtained in Example 1. The transformation was performed according to the TSS (transformation storage solution) method described in Proc. Natl. Acad. Sci. USA, 86, 2172–2175, 1989.

First, E. coli NM522 strain, the host bacteria, was cultured in 20 ml of an LB medium, and after the cells were collected by centrifugal separation they were suspended in 2 ml of TSS (LB medium at pH 6.5 containing 10% polyethylene glycol, 5% dimethylsulfoxide and 50 mM of Mg$^{2+}$). To 100 µl of the resulting suspension was added 20 µl of a mixture containing each plasmid obtained in the methods in (b)–(d), and the resulting mixture was treated at 0° C. for 30 minutes. Next, 0.9 ml of a TSS containing 20 mM of glucose was added thereto, culturing was conducted at 37° C. for 1 hour, and after further culturing at 37° C. in an LB agar medium containing ampicillin (50 µg/ml), there was obtained from the colony Escherichia coli NM522-pTRPCRPS-kil into which all of the plasmids had been introduced.

EXAMPLE 3

Cells from the colony of the transformant constructed in Example 2, Escherichia coli NM522-pTRPCRPS-kil (FERM BP-4244), were shake-cultured in 500 ml of an LB medium containing ampicillin (50 µg/ml) at 32° C. for 5 hours, and upon reaching the logarithmic growth phase they were induced by the addition of indoleacrylic acid (IAA). Three hours after induction the cells were collected by centrifugal separation and the medium was recovered. The medium was purified by affinity chromatography using a Toyo Pearl column on which phosphorylcholine had been immobilized via BSA (Japanese Patent Application Publication SHO 62-258390 (JP-A-62-258390), Japanese Patent Application Publication SHO 62-258399) (JP-A-62-258399). When the purified recombinant human CRP was analyzed by SDS polyacrylamide gel electrophoresis, it migrated to the same molecular weight location as naturally occurring CRP. Also, when the acrylamide gel in which the recombinant CRP had undergone electrophoresis was electrically transferred to a PVDF membrane and stained by the Western blotting method using each antibody obtained by immunizing each rabbit with natural CRP, the stained band was observed at the same location as the natural CRP.

Then, upon sequencing of 10 residues from the N-terminus of the recombinant CRP using a protein sequencer, it was found to agree with the natural occurring type.

EXAMPLE 4

Upon comparison of antiserum obtained by immunizing each rabbit with a mixture of the purified recombinant CRP prepared in Example 3 and Freund's complete adjuvant with antiserum obtained by immunizing each rabbit with CRP purified from human abdominal dropsy, the Becker's titer values were found to be the same (Table 1 below).

TABLE 1

| Antiserum | Becker's titer (mg/ml) | |
|---|---|---|
| | Natural CRP | Recombinant CRP |
| N1 | 5.2 | 5.1 |
| N2 | 4.1 | 4.3 |
| N3 | 5.4 | 4.8 |
| R3 | 4.7 | 4.6 |

TABLE 1-continued

| Antiserum | Becker's titer (mg/ml) | |
|---|---|---|
| | Natural CRP | Recombinant CRP |
| R5 | 6.7 | 5.7 |
| R7 | 6.4 | 8.7 |

When these antibodies were analyzed by Western blotting using CRP standard serum CA-7 (product of ATAB Co.), normal human serum CA-1 (product of ATAB Co.), CRP(−) serum and SAP, both exhibited exactly the same reactivity.

As mentioned above, the conventional preparation of human-derived proteins by gene recombinant technology has usually involved secretion into the periplasm of E. coli, but in the case of CRP, simple secretion into the periplasm has not provided the expression of the active type.

However, according to the present invention, by creating a plasmid by introducing the alkaline phosphatase signal peptide gene from E. coli just before the human CRP gene, and arranging the kil gene downstream from the human CRP gene so as to be under the control of the same promoter, the production of large amounts of human CRP by extracellular secretion, as well as the successful efficient production of highly pure human CRP, has been made possible for the first time.

In addition, the resulting recombinant CRP has exactly the same amino acid sequence as the naturally occurring form, and antiserum obtained by immunization therewith after purification exhibits exactly the same reactivity as antiserum obtained by immunization with the naturally occurring form, and therefore, when used as a reagent in clinical examinations, it is very useful as antigen for preparing antibodies for accurate assays of CRP levels in the blood or as a calibrator.

---

I claim:

1. A recombinant plasmid comprising an inducible bacterial promoter which is operably linked to a gene encoding a signal peptide operably linked to the gene encoding human C-reactive protein (CRP).

2. The recombinant plasmid according to claim 1, wherein said inducible bacterial promoter is the tryptophan promoter and said signal peptide is the *Escherichia coli* alkaline phosphatase signal peptide.

3. The recombinant plasmid according to claim 1, further comprising the kil gene.

4. The recombinant plasmid pTRPCRPS-kil having the pTRPCRPS-kil restriction map set forth in FIG. 1.

5. An *Escherichia coli* cell which is transformed with the recombinant plasmid of claim 1.

6. An *Escherichia coli* cell which is transformed with the recombinant plasmid of claim 2.

7. An *Escherichia coli* cell which is transformed with the recombinant plasmid of claim 3.

8. An *Escherichia coli* cell which is transformed with the recombinant plasmid pTRPCRPS-kil.

9. A method for producing recombinant human CRP which has the biological activity of non-recombinant human CRP, comprising culturing the *Escherichia coli* cell of claim 5 whereby said *Escherichia coli* cell expresses and secretes said recombinant human CRP which has the biological activity of non-recombinant human CRP, and recovering the secreted recombinant human CRP.

10. A method for producing recombinant human CRP which has the biological activity of non-recombinant human CRP, comprising culturing the *Escherichia coli* cell of claim 6 whereby said *Escherichia coli* cell expresses and secretes said recombinant human CRP which has the biological activity of non-recombinant human CRP, and recovering the secreted recombinant human CRP.

11. A method for producing recombinant human CRP which has the biological activity of non-recombinant human CRP, comprising culturing the *Escherichia coli* cell of claim 7 whereby said *Escherichia coli* cell expresses and secretes said recombinant human CRP which has the biological activity of non-recombinant human CRP, and recovering the secreted recombinant human CRP.

12. A method for producing recombinant human CRP which has the biological activity of non-recombinant human CRP, comprising culturing the *Escherichia coli* cell of claim 8 whereby said *Escherichia coli* cell expresses and secretes said recombinant human CRP which has the biological activity of non-recombinant human CRP, and recovering the secreted recombinant human CRP.

13. The method of claim 9, wherein said recombinant human CRP has the identical conformation as non-recombinant human CRP.

14. The method of claim 10, wherein said recombinant human CRP has the identical conformation as non-recombinant human CRP.

15. The method of claim 11, wherein said recombinant human CRP has the identical conformation as non-recombinant human CRP.

16. The method of claim 12, wherein said recombinant human CRP has the identical conformation as non-recombinant human CRP.

* * * * *